(12) United States Patent
Koga et al.

(10) Patent No.: US 10,337,880 B2
(45) Date of Patent: Jul. 2, 2019

(54) BURDEN ESTIMATION DEVICE AND BURDEN ESTIMATION METHOD

(71) Applicant: TOYOTA JIDOSHA KABUSHIKI KAISHA, Toyota-shi, Aichi-ken (JP)

(72) Inventors: Ko Koga, Tokyo (JP); Takuji Yamada, Musashino (JP); Keiko Suzuki, Tokyo (JP)

(73) Assignee: TOYOTA JIDOSHA KABUSHIKI, Toyota-shi (JP)

(*) Notice: Subject to any disclaimer, the term of this patent is extended or adjusted under 35 U.S.C. 154(b) by 0 days.

(21) Appl. No.: 15/832,253

(22) Filed: Dec. 5, 2017

(65) Prior Publication Data

US 2018/0156630 A1 Jun. 7, 2018

(30) Foreign Application Priority Data

Dec. 7, 2016 (JP) ................................. 2016-238045

(51) Int. Cl.

| G01C 21/36 | (2006.01) |
|---|---|
| A61B 5/18 | (2006.01) |
| G01C 21/34 | (2006.01) |
| G06F 17/30 | (2006.01) |
| G06F 16/635 | (2019.01) |
| G06F 16/22 | (2019.01) |

(52) U.S. Cl.
CPC ............ *G01C 21/3641* (2013.01); *A61B 5/18* (2013.01); *G01C 21/343* (2013.01); *G01C 21/3484* (2013.01); *G01C 21/3617* (2013.01); *G06F 16/22* (2019.01); *G06F 16/635* (2019.01)

(58) Field of Classification Search
CPC .............. G01C 21/3641; G01C 21/343; G01C 21/3484; G01C 21/3617; A16B 5/18; G06F 17/30312; G06F 17/30761
USPC ........................................................ 701/533
See application file for complete search history.

(56) References Cited

U.S. PATENT DOCUMENTS

2017/0154394 A1* 6/2017 Kan ....................... G06Q 50/28

FOREIGN PATENT DOCUMENTS

| JP | H04-43131 A | 2/1992 |
|---|---|---|
| JP | H08-173408 A | 7/1996 |
| JP | 2005-115482 A | 4/2005 |
| JP | 2006-026357 A | 2/2006 |
| JP | 2009-146185 A | 7/2009 |

(Continued)

*Primary Examiner* — Marthe Y Marc-Coleman
(74) *Attorney, Agent, or Firm* — Hunton Andrews Kurth LLP (57) ABSTRACT

A burden estimation device includes a state space configuration unit, a history learning unit acquiring from the user and storing in a storage unit data related to the burden on the user when the user travels to the destination along the travel route, an individual burden estimation unit evaluating a total travel burden and estimating an individual burden that is the burden on the user in correspondence with each of the states included in the state space through reinforcement learning that sets the total travel burden as a reward, and a total travel burden estimation unit estimating the total travel burden corresponding to an unknown travel route based on the estimated individual burden if the unknown travel route is set and the individual burden has already been estimated for at least some of the states defined in correspondence with the unknown travel route.

8 Claims, 9 Drawing Sheets

(56) References Cited

FOREIGN PATENT DOCUMENTS

| JP | 2009-293996 A | 12/2009 |
|---|---|---|
| JP | 2011-019552 A | 2/2011 |

\* cited by examiner

| Method of Travel | Purpose | Weather | Temperature | Road Environment (For Cars) | Pattern of Use | Frequent Level | Usage Time | Waiting Time (Traffic Congestion Time) | Calorie Consumption (Kcal) |
|---|---|---|---|---|---|---|---|---|---|
| $X_1$ | $X_2$ | $X_3$ | $X_4$ | $X_5$ | $X_6$ | $X_7$ | $X_8$ | $X_9$ | $X_{10}$ |
| Walking | Sightseeing | Sunny | Scorching | Lighted Road | Stand in Crowd | 0 | 5 | 5 | 10 |
| Bicycle | Business | Rain | Hot | Dark Road | Stand | 10 | 10 | 10 | 30 |
| Taxi | Club | Windy | Moderate | Narrow Road | Sit | 20 | 15 | 15 | 50 |
| Car | | Violent Winds | Cold | Wide Road | Walk Quickly | 30 | 20 | 20 | 75 |
| Train | | Torrent | Frigid | Mountain Road | Run | 40 | 30 | 30 | 100 |
| Bus | | Rainstorm | | | Drive Alone | 50 | 60 | 60 | 200 |
| Airplane | | | | | Drive with Family | 60 | 120 | 120 | 400 |
| Car Sharing | | | | | Drive with Friend | 70 | 180 | 180 | 600 |
| Car Rental | | | | | Family in Passenger Seat | 80 | 240 | 240 | 1000 |
| i-Road | | | | | Friend in Passenger Seat | 90 | 360 | 360 | 1500 |
| Shinkansen (Limited Express Train) | | | | | | 100 | 480 | 480 | 2000 |

Fig.3

| | State | Method of Travel $X_1$ | Purpose $X_2$ | Weather $X_3$ | Temperature $X_4$ | Road Environment $X_5$ | Pattern of Use $X_6$ | Frequent Level $X_7$ | Usage Time $X_8$ | Waiting Time $X_9$ | Calorie Consumption (Kcal) $X_{10}$ | Total Travel Burden $Y$ | Note |
|---|---|---|---|---|---|---|---|---|---|---|---|---|---|
| Known | S1 | Walking | Commuting | Sunny | Hot | — | Walk Quickly | 100 | 15 | 5 | 70 | 5 | Home to Station A |
| Known (Commuting 1) | S2 | Train | Commuting | Sunny | Moderate | — | Stand | 100 | 15 | 5 | 80 | | Station A to Station B |
| Known (Commuting 1) | S3 | Train | Commuting | Sunny | Moderate | — | Sit | 100 | 20 | 0 | 50 | | Station B to Station C |
| Known (Commuting 1) | S4 | Walking | Commuting | Sunny | Hot | — | Walk Quickly | 100 | 10 | 0 | 70 | | Station C to Workplace |
| Known (Shopping 1) | S5 | Walking | Shopping | Sunny | Hot | — | Walk Quickly | 100 | 15 | 5 | 70 | 2 | Home to Station A |
| Known (Shopping 1) | S6 | Train | Shopping | Rain | Moderate | — | Stand | 100 | 6 | 5 | 30 | | Station A to Station D |
| Unknown (Facility A) | S7 | Walking | Travel | Sunny | Hot | — | Walk Quickly | 100 | 15 | 0 | 70 | ? | Home to Station A |
| Unknown (Facility A) | S8 | Train | Travel | Sunny | Moderate | — | Stand In Crowd | 30 | 21 | 5 | 80 | | Station A to Station E |
| Unknown (Facility A) | S9 | Train | Travel | Sunny | Moderate | — | Stand In Crowd | 0 | 15 | 5 | 50 | | Station E to Station F |
| Unknown (Facility A) | S10 | Limited Express Train | Travel | Sunny | Moderate | — | Sit | 0 | 65 | 6 | 150 | | Station F to Station G |
| Unknown (Facility A) | S11 | Bus | Travel | Sunny | Moderate | — | Sit | 0 | 30 | 30 | 160 | | Station G to Facility A |

| | | State | Total Travel Burden | Estimated Individual Burden | Dispersion | Estimated Burden |
|---|---|---|---|---|---|---|
| | | | Y | V (s) | ΔV (s) | Y_ |
| Known | Commuting 1 | S1 | 5 | 1.5 | 0.2 | 5 |
| | | S2 | | 1 | 0.3 | |
| | | S3 | | 1 | 0.2 | |
| | | S4 | | 1.5 | 1.5 | |
| | Shopping 1 | S5 | 2 | 1.5 | 0.2 | 2.2 |
| | | S6 | | 0.7 | 1.1 | |
| Unknown | Facility A | S7 | ? | 2 | 0.4 | 14 |
| | | S8 | | 3 | 0.3 | |
| | | S9 | | 1 | 1 | |
| | | S10 | | 4 | 1.8 | |
| | | S11 | | 4 | 5 | |

Fig.6

| User ID | State | Estimated Individual Burden |
|---|---|---|
| ID1 | S1 | 1.4 |
| | S2 | 1.1 |
| | S3 | 1.1 |
| | ⋮ | ⋮ |
| ID2 | S1 | 1.6 |
| | S2 | 1.2 |
| | S3 | 1.3 |
| | ⋮ | ⋮ |
| ID3 | S1 | 1.7 |
| | S2 | 1.4 |
| | S3 | 1.3 |
| | ⋮ | ⋮ |
| ⋮ | ⋮ | ⋮ |

BURDEN ESTIMATION DEVICE AND BURDEN ESTIMATION METHOD

CROSS-REFERENCE TO RELATED APPLICATION

The present application claims priority to Japanese Patent Application No. 2016-238045 filed on Dec. 7, 2016, which is incorporated herein by reference in its entirety.

BACKGROUND ART

The present invention relates to a burden estimation device and a burden estimation method for estimating the burden on a user when the user uses travels by using a plurality of methods of travel.

Japanese Laid-Open Patent Publication No. 2009-146185 describes an example of a fatigue level determination device that calculates an operation fatigue level per unit time, which is based on a vehicle operating amount of the driver, and a behavior fatigue level per unit time, which is based on information related to the vehicle behavior. Specifically, for example, the operation fatigue level per unit time is lower when the vehicle speed is low than when the vehicle speed is fast because the steering wheel or brake can easily be operated. In addition, the behavior fatigue level per unit time is higher when the vehicle speed is low than when the vehicle speed is high because the driver is likely to be driving in an urban area or the like under complicated road situations. Furthermore, the fatigue level determination device estimates the fatigue level of the driver by sequentially accumulating the sum of the operation fatigue level per unit time and behavior fatigue level per unit time from when the driver starts to drive.

The fatigue level determination device simply estimates the driver fatigue level when the driver is driving the vehicle. The fatigue level determination device cannot calculate the fatigue level of a user when the user is using traveling using a plurality of methods of travel in addition to a vehicle. Also, it is unknown whether the calculated fatigue appropriately reflects the fatigue and burden of the user. In addition, fatigue means only physical fatigue such as muscle fatigue and operation burden, and burden means the sum of physical and mental fatigue.

On the other hand, biological signals of a user may be used to calculate the fatigue level of a user when the user is traveling by using a plurality of methods of travel. However, the fatigue level calculated from user biological signals would only be a fatigue level reflecting consumption of the physical strength of the user. This would not necessarily correspond to the burden on the user.

SUMMARY OF THE INVENTION

It is an object of the present invention to provide a burden estimation device and a burden estimation method capable of estimating the burden on the user when the user is using a plurality of methods of travel to travel.

To achieve the above object, one aspect of the present invention is a burden estimation device including a state space configuration unit that defines a state space, wherein the state space is defined in correspondence with a travel route along which a user travels to a destination while changing methods of travel, the state space includes states that correspond to the travel route along which the user travels and in which the states are continuous over time, each of the states is defined by combining multiple types of data that characterize burden on the user as the user travels, a history learning unit configured to acquire from the user and store in a storage unit data related to the burden on the user when the user travels to the destination along the travel route, an individual burden estimation unit configured to evaluate a total travel burden as a comprehensive burden on the user when the user travels to the destination along the travel route based on the data related to the burden stored in the storage unit, and the individual burden estimation unit is further configured to estimate an individual burden that is the burden on the user in correspondence with each of the states included in the state space through reinforcement learning that sets the total travel burden as a reward, and a total travel burden estimation unit configured to estimate the total travel burden corresponding to an unknown travel route based on the estimated individual burden if the unknown travel route is set and the individual burden has already been estimated for at least some of the states defined in correspondence with the unknown travel route.

To achieve the above object, one aspect of the present invention is a method for estimating burden, the method including defining a state space, wherein the state space is defined in correspondence with a travel route along which a user travels to a destination while changing methods of travel, the state space includes states that correspond to the travel route along which the user travels and in which the states are continuous over time, each of the states is defined by combining multiple types of data that characterize burden on the user as the user travels, acquiring, from the user, and storing, in a storage unit, data related to the burden on the user when the user travels to the destination along the travel route, evaluating a total travel burden as a comprehensive burden on the user when the user travels to the destination along the travel route based on the data related to the burden stored in the storage unit, estimating an individual burden that is the burden on the user in correspondence with each of the states included in the state space through reinforcement learning that sets the total travel burden as a reward, and estimating the total travel burden corresponding to an unknown travel route based on the estimated individual burden if the unknown travel route is set and the individual burden has already been estimated for at least some of the states defined in correspondence with the unknown travel route.

To achieve the above object, one aspect of the present invention is a burden estimation device including circuitry, wherein the circuitry is configured to define a state space, wherein the state space is defined in correspondence with a travel route along which a user travels to a destination while changing methods of travel, the state space includes states that correspond to the travel route along which the user travels and in which the states are continuous over time, each of the states is defined by combining multiple types of data that characterize burden on the user as the user travels, acquire, from the user, and store, in a storage unit, data related to the burden on the user when the user travels to the destination along the travel route, evaluate a total travel burden as a comprehensive burden on the user when the user travels to the destination along the travel route based on the data related to the burden stored in the storage unit, estimate an individual burden that is the burden on the user in correspondence with each of the states included in the state space through reinforcement learning that sets the total travel burden as a reward, and estimate the total travel burden corresponding to an unknown travel route based on the estimated individual burden if the unknown travel route is set and the individual burden has already been estimated for at least some of the states defined in correspondence with the unknown travel route.

BRIEF DESCRIPTION OF DRAWINGS

The invention, together with objects and advantages thereof, may best be understood by reference to the following description of the presently preferred embodiments together with the accompanying drawings in which.

DETAILED DESCRIPTION OF THE INVENTION

A burden estimation device according to one embodiment will now be described.

The burden estimation device is configured by a center that manages information of a plurality of users owning portable information terminals. The center defines a state space as a set of states. Each state is defined by associating, for example, various types of data that characterize the burden on a user as the user travels, such as the type of methods of travel, the purpose for traveling, and the weather when traveling. In addition, the center defines a behavior space as a set of actions that can be realized for each state (for example, methods of travel that can be proposed). The methods of travel include, but are not limited to, walking, bicycle, taxi, car, train, bus, airplane, car sharing, car rental, i-Road (registered trademark), and Shinkansen (limited express train). Furthermore, when a user arrives at a destination of a travel route, the center performs a dialog with a user regarding burden through the portable information terminal. Specifically, a user inputs, in an interactive format, data related to burden by operating the portable information terminal. The center acquires the burden of the user for traveling along the travel route as a total travel burden based on a dialog input history that is the data input by user. In addition, the center executes reinforcement learning to estimate individual burdens for each state included in the state space by setting the total travel burden of the user as a reward. Furthermore, when the center receives a request for the burden related to a travel route unknown to a user from the portable information terminal, the center determines whether or not there is data for the individual burden for each state included in this unknown travel route. Moreover, when data for the individual burden related to every state included in the unknown travel route has been obtained in advance, the sum of the individual burdens is provided as a total travel burden for the entire unknown travel route to the user through the portable information terminal.

First, the configuration of the device for this embodiment will be described with reference to the drawings.

Figure 1:
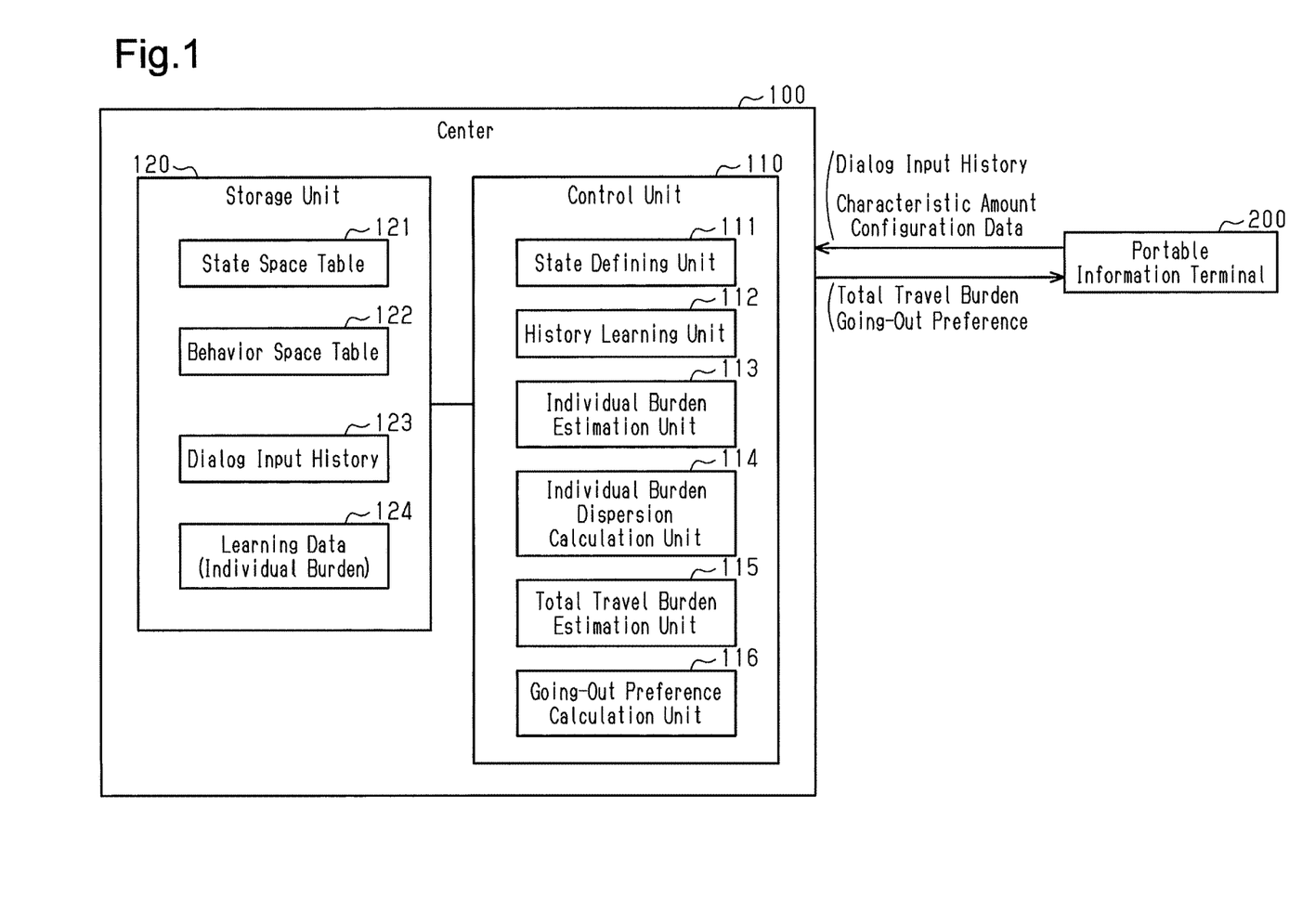
FIG. 1 is a schematic block diagram illustrating the configuration of a burden estimation device according to one embodiment.

As illustrated in FIG. 1, a center 100 includes a control unit 110 and a storage unit 120. The control unit 110 controls various processes including a user burden estimation process. The storage unit 120 stores various programs including a burden estimation program executed by the control unit 110 during the user burden estimation process or various types of data read and/or written by the control unit 110 during execution of various programs. Here, the various types of data stored in the storage unit 120 include a state space table 121 that defines a state space, a behavior space table 122 that defines a behavior space, a dialog input history 123 of the user, and learning data 124 related to individual burdens of each state. The center 100 may be configured as a circuitry including 1) one or more dedicated hardware circuits such as an application specific integrated circuit (ASIC), 2) one or more processors operated by a computer program (software), and 3) a combination of the above. The processor includes a central processing unit (CPU) and a memory such as a random access memory (RAM) and a read-only memory (ROM). The memory stores program codes or instructions configured to have the CPU execute processing. The memory, that is, computer readable medium includes any type of usable media that can be accessed by a versatile or dedicated computer.

Figure 2:
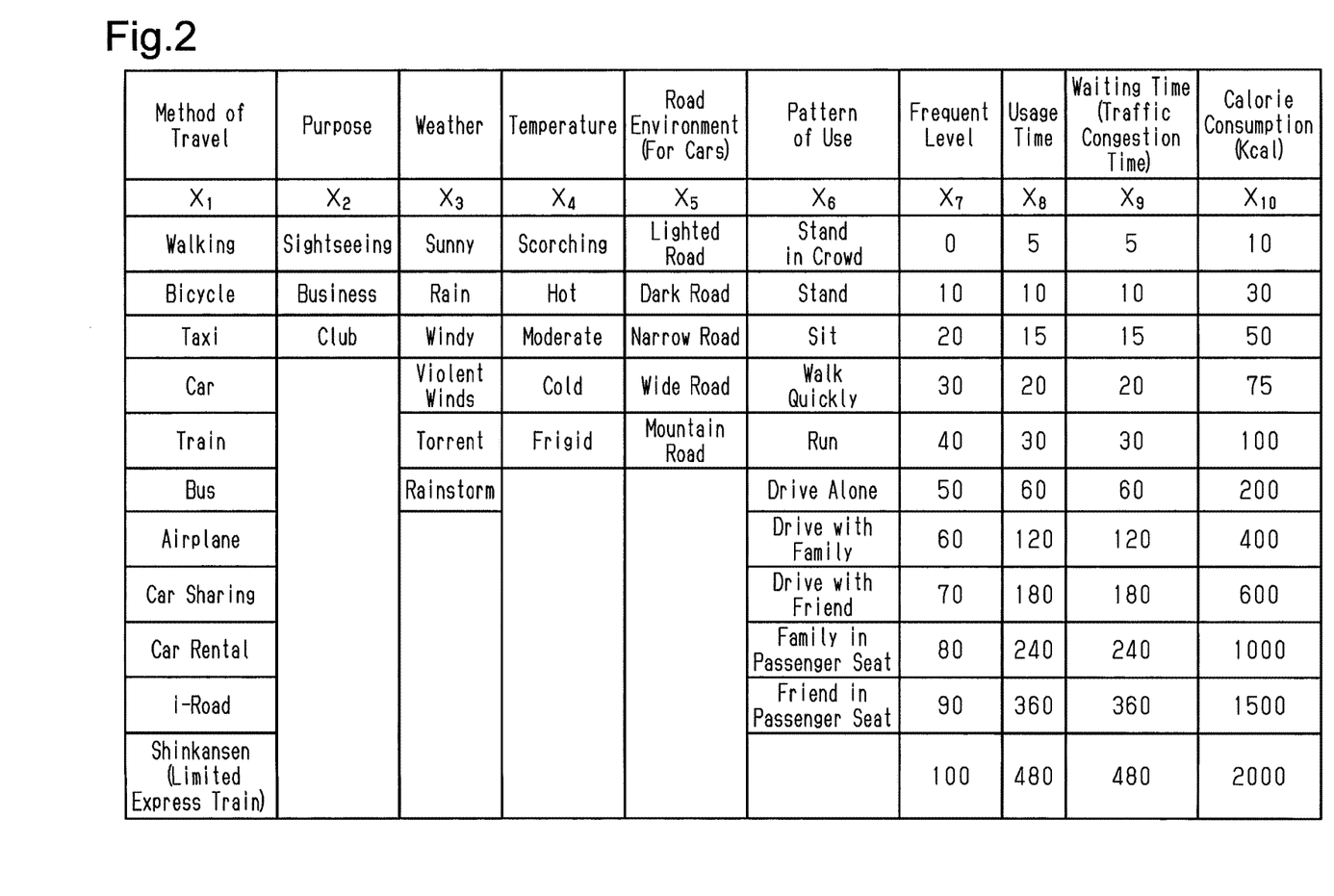
FIG. 2 is a diagram illustrating a plurality of exemplary characteristic amounts used to define states included in a state space.

FIG. 2 illustrates a plurality of exemplary characteristic amounts used to define states included in the state space. Here, a characteristic amount is a factor for characterizing a burden generated when a user travels and is recorded in advance to the center 100. In the example of FIG. 2, the characteristic amount includes type of the method of travel, travel purpose, weather, temperature, road condition for cases in which the method of travel is a vehicle, pattern of use of the method of travel, frequent level, usage time of the method of travel, waiting time until using the method of travel, and calorie consumption during use of method of travel. As illustrated in FIG. 2, for example, the characteristic amount of "purpose" includes attributes such as sightseeing, business, and club. The characteristic amount of "temperature" includes attributes such as scorching, hot, moderate, cold, and frigid. In addition, the state space table 121 defines a state space including a set of states, and each state is defined by a combination of the various attributes listed in FIG. 2.

As illustrated in FIG. 1, the control unit 110 executes various programs stored in the storage unit 120 of the center 100 to function as a state defining unit 111, a history learning unit 112, an individual burden estimation unit 113, an individual burden dispersion calculation unit 114, a total travel burden estimation unit 115, and a going-out preference calculation unit 116. The state defining unit 111 functions as a state space configuration unit.

The state defining unit 111 determines the current state of the user based on data related to the characteristic amount cyclically transmitted from the portable information terminal 200 to the center 100. The user's current state is included in the state space.

After the user sets a travel route using the portable information terminal 200, the history learning unit 112 instructs the portable information terminal 200 to have a dialog with the user when the user arrives at the destination of the set travel route. In addition, the history learning unit 112 stores a dialog input history 123 in the storage unit 120 when receiving the dialog input history 123 that is input to the portable information terminal 200 by the user. As described above, the characteristic amounts include the frequent level. In a case where the frequent level for a state included in a certain travel route is relatively high, the user is most likely often using the travel route. If the user is often using a certain travel route, the history learning unit 112 instructs the portable information terminal 200 to have a dialog with the user at a frequency of once out of a number of times the user uses the travel route. That is, if the frequent level for the travel route of the user is greater than or equal to a predetermined threshold value, the history learning unit 112 instructs the portable information terminal 200 to have a dialog with the user at a frequency of once out of a number of times when the user arrives at the destination of the travel route. Therefore, the history learning unit 112 acquires data related to the total travel burden from the user at a frequency of once out of a number of times when the user arrives at the destination of the travel route.

The individual burden estimation unit 113 evaluates the total travel burden of the user when the user travels along the travel route based on the dialog input history 123 read from the storage unit 120. In addition, the individual burden estimation unit 113 executes the Monte Carlo method, which is a type of reinforcement learning method, by setting the total travel burden of the user as a reward. In this case, the individual burden estimation unit 113 equally divides the total travel burden of the user during traveling along the travel route by the number of states included in the travel route to estimate an individual burden. The individual burden estimation unit 113 may divide the total travel burden of the user during traveling along the travel route in accordance with the ratio of the usage time of the method of travel for each state in the travel route to estimate the individual burden of each state. In addition, the individual burden estimation unit 113 stores the individual burden of each state estimated in this manner as the learning data 124 in the storage unit 120. The individual burden estimation unit 113 records the estimation value to the storage unit 120 as a log whenever the individual burden of each state is estimated in order to estimate an average value of the recorded estimated values of the individual burden as the individual burden of each state.

The individual burden dispersion calculation unit 114 calculates dispersion as one example of an index indicating the scattered level of the estimated individual burden estimation value whenever the individual burden estimation value of each state is stored in the storage unit 120 as the learning data 124. The scattered level of the individual burden estimation value reflects the reliability of the individual burden estimation value for each state. The reliability of the individual burden estimation value is higher when the scattered level is smaller. In addition, if the dispersion of the estimated values of the individual burden corresponding to the current state of the user is relatively large, the history learning unit 112 instructs the portable information terminal 200 to have a dialog with the user in order to inquire the user on the individual burden corresponding to the current state.

Cases in which the dispersion of the individual burden estimation value is large include a case in which the individual burden of the user is unknown. For this reason, if a state in which the individual burden of the user is unknown is included in the travel route, the history learning unit 112 instructs the portable information terminal 200 to have a dialog with the user when the user state changes to a state in which the individual burden is unknown.

If a user sets an unknown travel route with the portable information terminal 200, the total travel burden estimation unit 115 estimates the total travel burden of the user when the user travels along the unknown travel route in response to a request from the portable information terminal 200. In order to estimate the total travel burden of the unknown travel route, the total travel burden estimation unit 115 first checks whether or not individual burden has been estimated in advance as the learning data 124 for each state included in the unknown travel route. In addition, if the individual burden has been estimated in advance for all of the states included in the unknown travel route, the total travel burden estimation unit 115 estimates the sum of the individual burden as the total travel burden of the user when traveling along the unknown travel route.

When a request for a going-out preference, which serves as an index indicating the preference of a user to go out, is received from the portable information terminal 200, the going-out preference calculation unit 116 calculates the going-out preference of the user based on the individual burden of the user stored in the storage unit 120. In this case, in order to calculate the going-out preference, the going-out preference calculation unit 116 reads burden levels from the storage unit 120 of a plurality of users who go out in the same manner and compares the burden levels. In addition, the going-out preference calculation unit 116 calculates the going-out preference to be smaller if the burden of the requesting user is larger than the burden of other users. Then, the going-out preference calculation unit 116 transmits the going-out preference calculated in this manner to the portable information terminal 200 of the requesting user.

Figure 3:
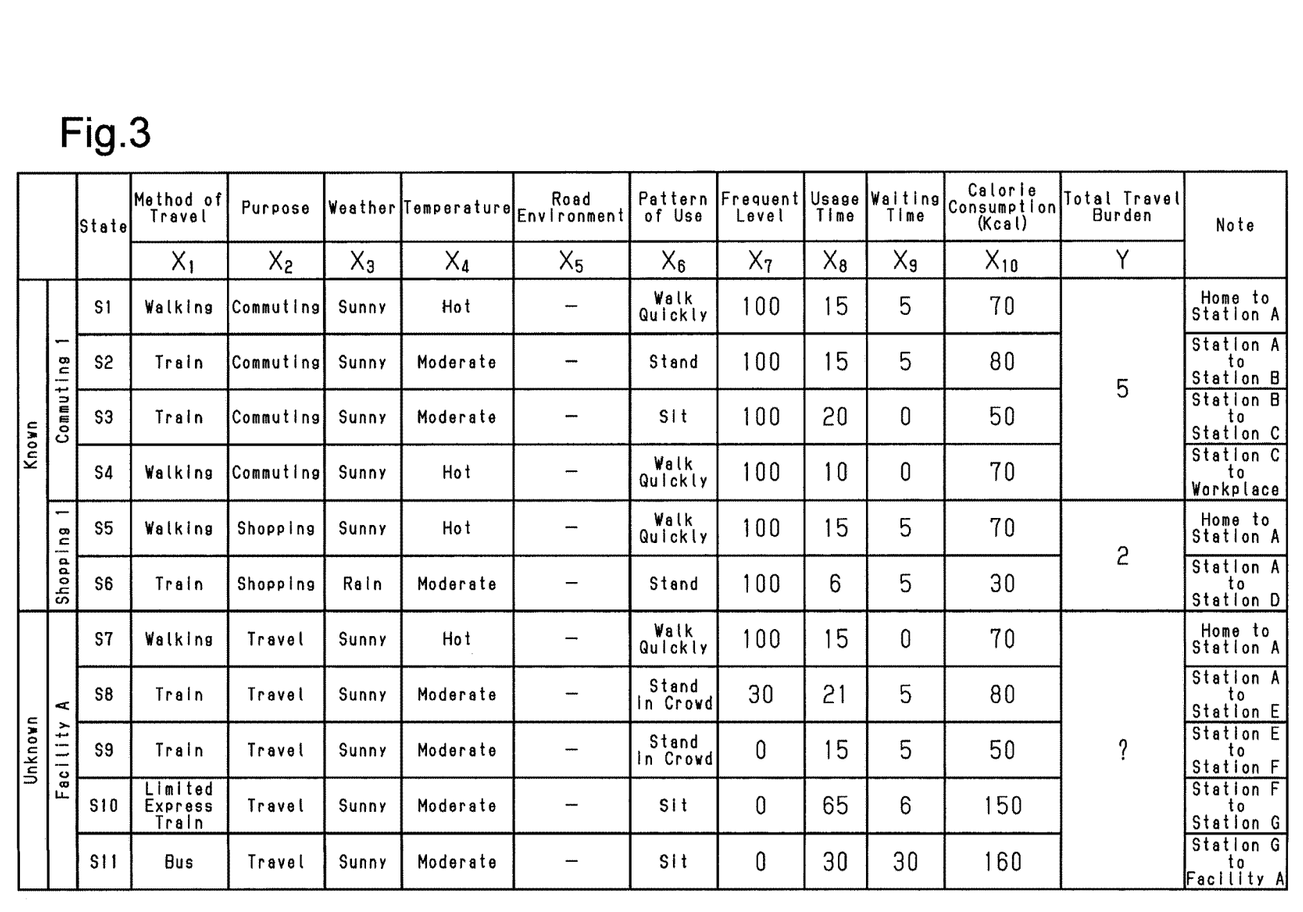
FIG. 3 is a diagram illustrating a plurality of states included in each travel route in addition to characteristic amounts of each state and user total travel burden.

FIG. 3 is a data table illustrating a travel route of the user, a plurality of states included in the travel route, and total travel burdens of the user when traveling along the travel route. In the example of FIG. 3, the known travel routes that have been used by a user in the past includes a travel route used in a customary manner when commuting to work and a travel route used in a customary manner when going shopping.

A commuting travel route includes a travel section in which the user walks from "home" to "station A," a travel section in which the user takes a train from "station A" to "station B," a travel section in which the user transfers trains and goes from "station B" to "station C," and a travel section in which the user walks from "station C" to "workplace." States included in the commuting travel route are defined by taking into account conditions surrounding the user when traveling through each travel section. Furthermore, the total travel burden of the user when traveling along the commuting travel route is set to "known" because inquiries were made to the user in the past from the center 100 using the portable information terminal 200 when the travel route was used.

In the same manner, a travel route for shopping includes a travel section in which the user walks from "home" to "station A" and a travel section in which the user takes a train from "station A" to "station D." In addition, states included in the shopping travel route are defined by taking into account conditions surrounding the user when traveling through each travel section. Furthermore, the total travel burden of the user when traveling along the shopping travel route is also set to "known" because inquiries were made in the past from the center 100 with the portable information terminal 200 when the travel route was used.

In this example, the commuting travel route and the shopping travel route both include the travel section from "home" to "station A." In addition, the conditions surrounding the user such as the weather, the temperature, and the pattern of use when traveling through these travel sections are also the same. However, the travel purpose differs between the commuting and the shopping travel sections. Thus, different states are defined for these travel sections. More specifically, the physical consumption level of the user when traveling along through these travel sections are considered to be substantially equal. However, the burden on the user differs depending on the travel purpose. Therefore, different states are defined for these travel routes.

In the example of FIG. 3, an unknown travel route that has not been used by a user in the past is also included as a travel route in which facility A is set as a destination. The unknown travel route includes a travel section in which the user walks from "home" to "station A," a travel section in which the user takes a train from "station A" to "station E," a travel section in which the user transfers trains and goes from "station E" to "station F," a travel section in which the user transfers trains and takes a limited express train from "station F" to "station G," and a travel section in which the user takes a bus from "station G" to "facility A." In this case, the total travel burden when the user travels along the unknown travel route is set to "unknown" because the user has not used this travel route in the past and there has been no inquiries to the user regarding the total travel burden.

Figure 4:
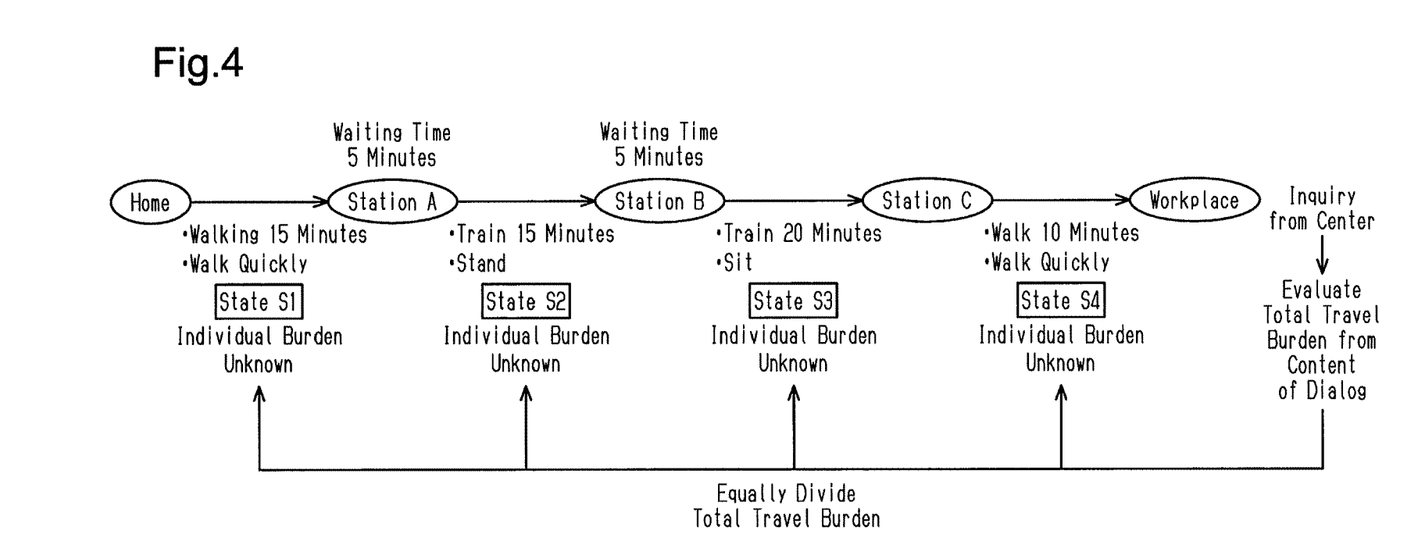
FIG. 4 is a diagram illustrating the flow of a process for estimating individual burdens of each state included in the travel route.

FIG. 4 illustrates a process flow when the center 100 estimates the individual burden of each state included in the travel route by exemplifying the commuting travel route of FIG. 3. In the example of FIG. 3, the commuting travel route includes the travel section from "home" to "station A," the travel section from "station A" to "station B," the travel section from "station B" to "station C," and the travel section from "station C" to "workplace," and the individual burden for the states respectively corresponding to the travel sections is not known. More specifically, in this embodiment, the individual burden of the user when traveling through a travel section is not always inquired whenever a user passes through the travel section. Rather, the center 100 inquires the user about the total travel burden using the portable information terminal 200 when the user arrives at the destination of the travel route (in this example, "workplace"). In addition, the center 100 evaluates the total travel burden of the user based on the dialog input history 123 received from the user. In this case, the total travel burden serving as an evaluation subject is not the burden of each travel section in the travel route. Rather, the total travel burden is the burden of the entire travel route. In addition, if the center 100 obtains an evaluation result of the total travel burden of the user, the total travel burden that is the evaluation result is equally divided by the number of states included in the travel route to estimate the individual burden of each state.

Figure 5:
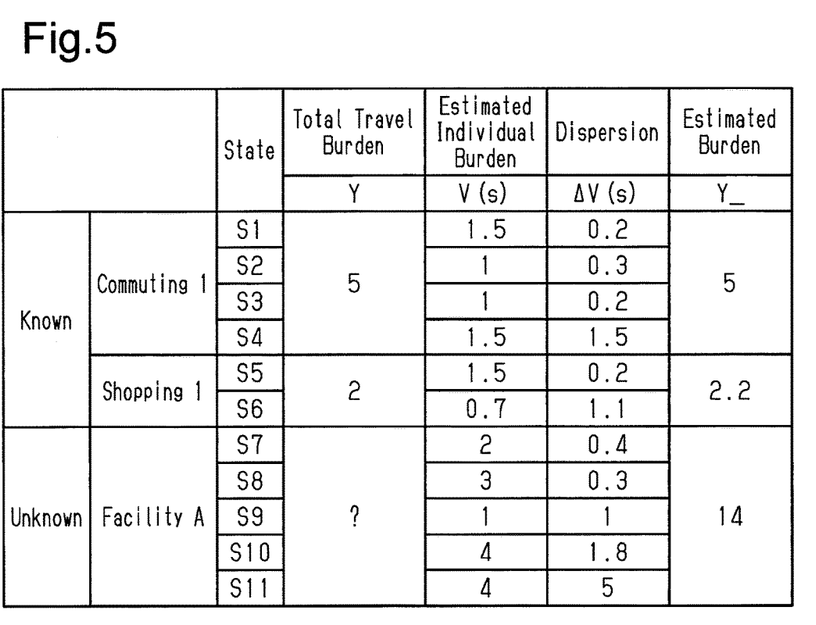
FIG. 5 is a diagram illustrating one example of the setting contents of a data table used to estimate burdens when a user is traveling along an unknown travel route.

FIG. 5 is a data table of a list of the individual burdens of each state included in each travel route of FIG. 3 estimated from various travel routes of the user including the commuting travel route and the shopping travel route. In the example of FIG. 5, the individual burdens of the states included in the commuting travel route and the shopping travel route are known and have been estimated by equally dividing the total travel burden, which is the burden of the user for the entire travel route, by the number of states included in the travel route, as illustrated in FIG. 4. Different travel routes may include the same state. However, the individual burden of the state may have a value that differs between the travel routes. Nevertheless, by accumulating the estimated values of the individual burden for each state included as the user repeatedly travels along the travel route, the individual burdens of each state will approach ideal value that is in accordance with the actual situation of the user.

In the example of FIG. 5, states S1 and S2 included in the commuting travel route have different individual burdens, and states S5 and S6 included in the shopping travel route have different individual burdens. This is because the individual burdens of these states are calculated based on the total travel burdens of a plurality of travel routes. More specifically, if a number of travel routes include the same state, the individual burden of each state is calculated based on the total travel burdens of the travel routes. In addition, in the example of FIG. 5, in either one of the commuting travel route and the shopping travel route, the total travel burden obtained by inquiring the user when traveling along the travel route is substantially equal to the total travel burden obtained by adding the estimated values of the individual burden for the states included in the travel route.

In the example of FIG. 5, the dispersion of the estimated values of the individual burden recorded as logs for each state is also calculated. In this example, for states S1 to S3 included in the commuting travel route, the dispersion of the estimated values of the individual burden is a relatively small value. For this reason, if the user uses this travel route to commute, and the situation of the user corresponds to states S1 to S3 when traveling along through these travel sections, the center 100 does not inquire the user of the individual burden. For state S4 in the commuting travel route, the dispersion of the individual burden estimation value is a relatively large value. For this reason, if the user travels along this travel route to commute and the situation of the user is state S4 when traveling through the corresponding travel section, the center 100 inquires the user on the individual burden when the user passes through this travel section. In the same manner, for the shopping travel route, it is determined whether or not to inquire the individual burden of each state based on the dispersion of the estimated values of the individual burden for the states included in the travel route.

In the example of FIG. 5, the individual burdens are also estimated for each state included in the unknown travel route of FIG. 3. The unknown travel route is a route along which a user has not yet traveled. If the user has traveled along another travel route that includes one or more states of the unknown travel route, the individual burdens of such states have been already estimated. In the example of FIG. 5, the individual burdens are estimated for all of the states included in the unknown travel route based on the individual burdens or the like that have been already estimated. In this case, even when the total travel burden of the user when traveling along an unknown travel route is unknown, it is possible to estimate the total travel burden of the unknown travel route by adding the individual burdens of the states included in the unknown travel route.

Figure 6:
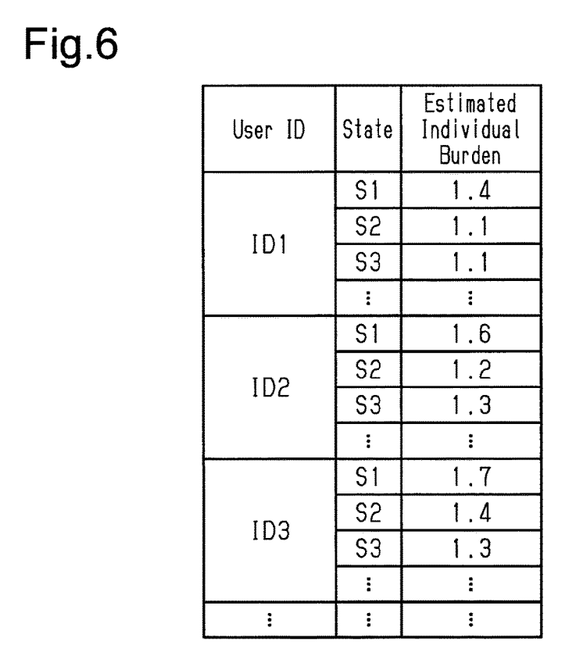
FIG. 6 is a diagram illustrating an example of individual burdens of each state included in the state space for each of a plurality of users.

FIG. 6 is a data table of a list of the estimated values of the individual burden of each state obtained for a plurality of users. As illustrated in the example of FIG. 6, a common tendency is recognized in the relationship of the individual burdens between different users for each state. That is, in this example, the relationship of the individual burdens of three users is compared for each of states S1 to S3. The users represented by "ID3," "ID2," and "ID1" are listed in order from the one having the higher individual burden. Although there is a slight difference in the individual burden for each state, a user who prefers to go out feels at ease regardless of the situation when traveling. Therefore, the burden on the user when traveling tends to be relatively low.

Figure 7:
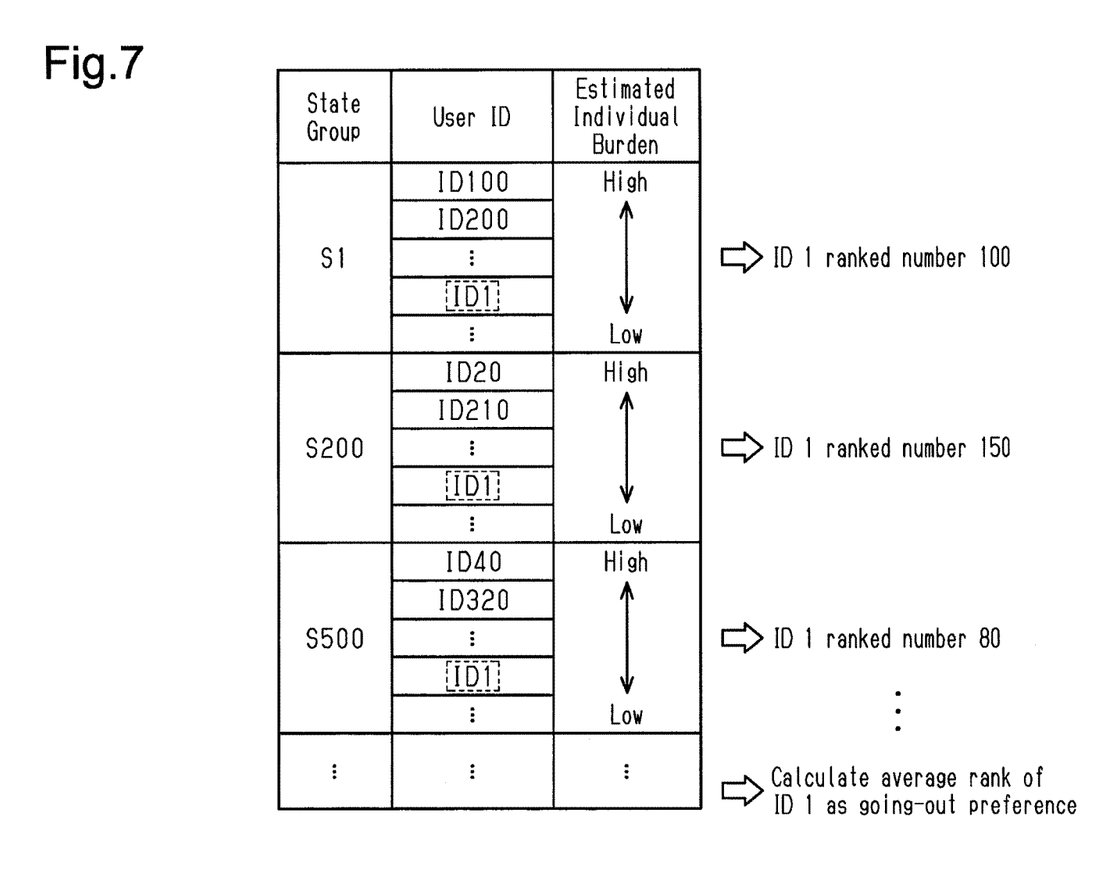
FIG. 7 is a diagram illustrating a process flow for calculating a going-out preference of a user.

Next, a process for calculating a going-out preference using the going-out preference calculation unit 116 will be described with reference to FIG. 7. As illustrated in FIG. 7, the going-out preference calculation unit 116 first selects a state group in order to calculate the going-out preference. The state group includes a plurality of states. In the example of FIG. 7, the state group includes states S1, S200, and S500. Further, the going-out preference calculation unit 116 sorts the users in in order from the ones having a higher estimated individual burden for each state included in the selected state group. In addition, the going-out preference calculation unit 116 calculates the ranks of the users subject to the going-out preference calculation from the higher estimated individual burden of each state included in the selected state group. Further, the going-out preference calculation unit 116 calculates an average value of the user ranks for the states included in the selected state group as a going-out preference. The estimated values of the individual burden are not necessarily obtained for all of the states included in the state space for each user. For this reason, the number of users compared for each state included in the state group is not always the same. Thus, the going-out preference calculation unit 116 may calculate the user's going-out preference after weighting the ranks of the users for each state taking into account the number of users compared for each state included in the state group.

Next, a processing sequence of the individual burden update process executed by the center 100 according to this embodiment will be described in detail. The center 100 executes the individual burden update process for each state included in the travel route when it receives the travel route and the destination information input to the portable information terminal 200 by a user.

Figure 8:
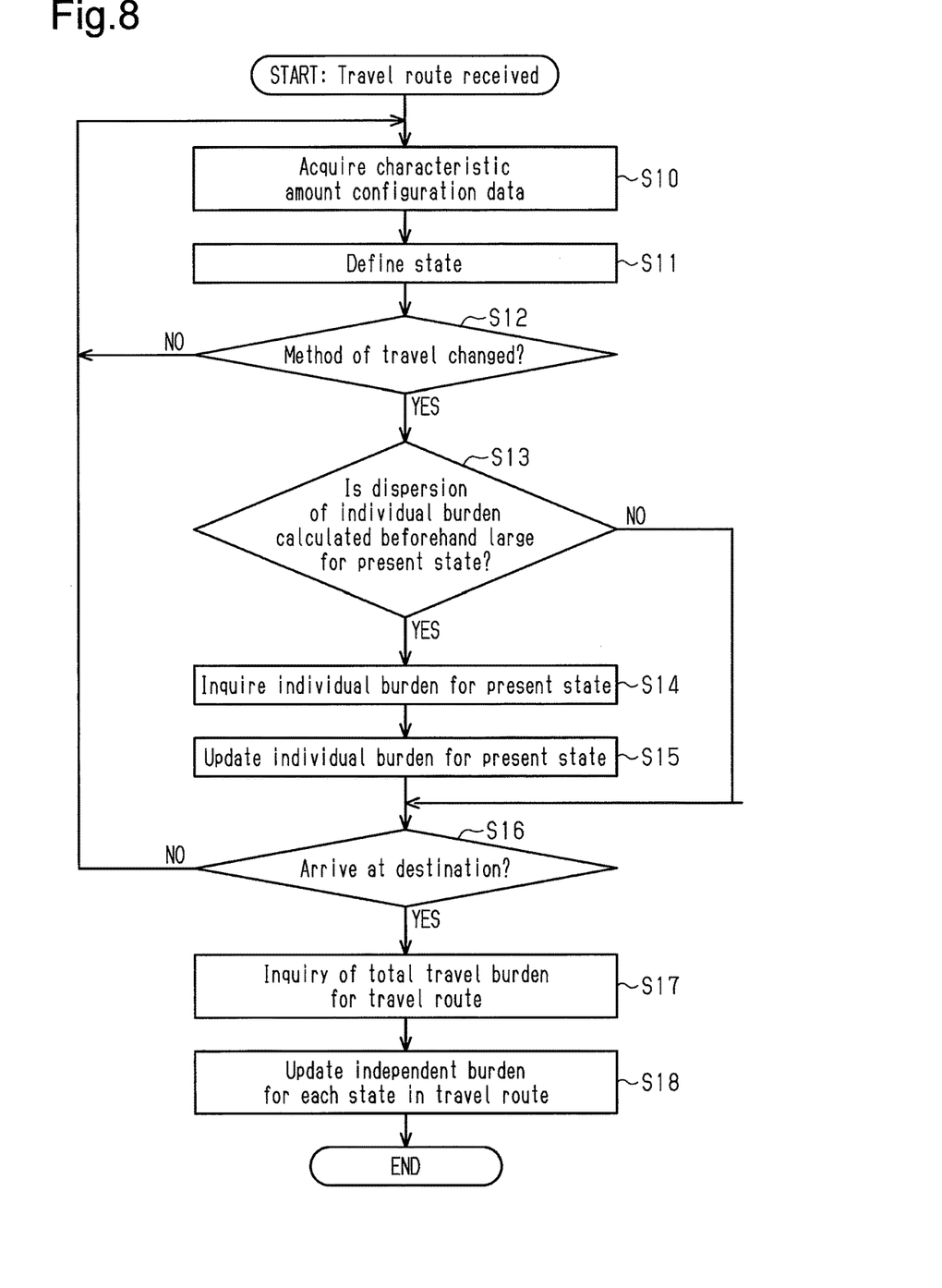
FIG. 8 is a flowchart illustrating an individual burden update process executed by the burden estimation device of FIG. 1.

First, as illustrated in FIG. 8, the center 100 acquires various types of data used to determine the current state of the user as characteristic amount configuration data from the portable information terminal 200 via the state defining unit 111 (step S10).

Subsequently, the center 100 determines whether or not any one of the states defined in the state space table 121 matches the current state of the user using the state defining unit 111 based on the characteristic amount configuration data acquired in step S10 (step S11).

Then, the center 100 determines whether or not the method of travel used by the user has changed based on the information acquired from the portable information terminal 200 (step S12). In addition, if it is determined that the method of travel has not changed (NO in step S12), the center 100 returns to step S10. Then, steps S10 to S12 are repeated until the method of travel changes.

If it is determined that the method of travel has changed (YES in step S12), the center 100 reads the dispersion of the individual burden estimation value corresponding to the current state of the user from the storage unit 120 via the history learning unit 112. In addition, the center 100 determines whether the dispersion of the estimated values of the individual burden read in this manner is greater than or equal to a predetermined threshold value (step S13). That is, the center 100 determines whether or not the scattering of the individual burdens calculated in advance is large for the current state of the user using the history learning unit 112 (step S13).

If it is determined that the scattering of the individual burdens is large (YES in step S13), the history learning unit 112 of the center 100 inquires the user of the individual burden for traveling corresponding to the current state of the user with the portable information terminal 200 (step S14). In addition, the center 100 updates the individual burden obtained through the inquiry made to the user as the individual burden corresponding to the current state of the user (step S15) and then proceeds to step S16. If it is determined that the scattering of the individual burden is small in step S13 (NO in step S13), the center 100 proceeds to step S16 without performing steps S14 and S15.

In step S16, the center 100 determines whether or not the user has received a signal indicating that the user has arrived at the destination from the portable information terminal 200. If the user has not arrived at the destination (NO in step S16), the center 100 returns to step S10 and repeats steps S10 to S16.

If a signal indicating that the user has arrived at the destination is received from the portable information terminal 200 (YES in step S16), the history learning unit 112 of the center 100 inquires the user on the total travel burden for traveling along the travel route using the portable information terminal 200 (step S17).

Then, the center 100 obtains the estimated value of the individual burden for each state by equally dividing the total travel burden obtained through an inquiry to the user by the number of states included in the travel route and updates the existing value of the individual burden based on the estimated value (step S18). Then, the individual burden update process of FIG. 8 is terminated.

Next, a processing sequence of a total travel burden estimation process for an unknown travel route executed by the center 100 according to this embodiment will be described in detail. The center 100 executes the total travel burden estimation process for an unknown travel route in response to a request from the portable information terminal 200 when a user sets an unknown travel route using the portable information terminal 200.

Figure 9:
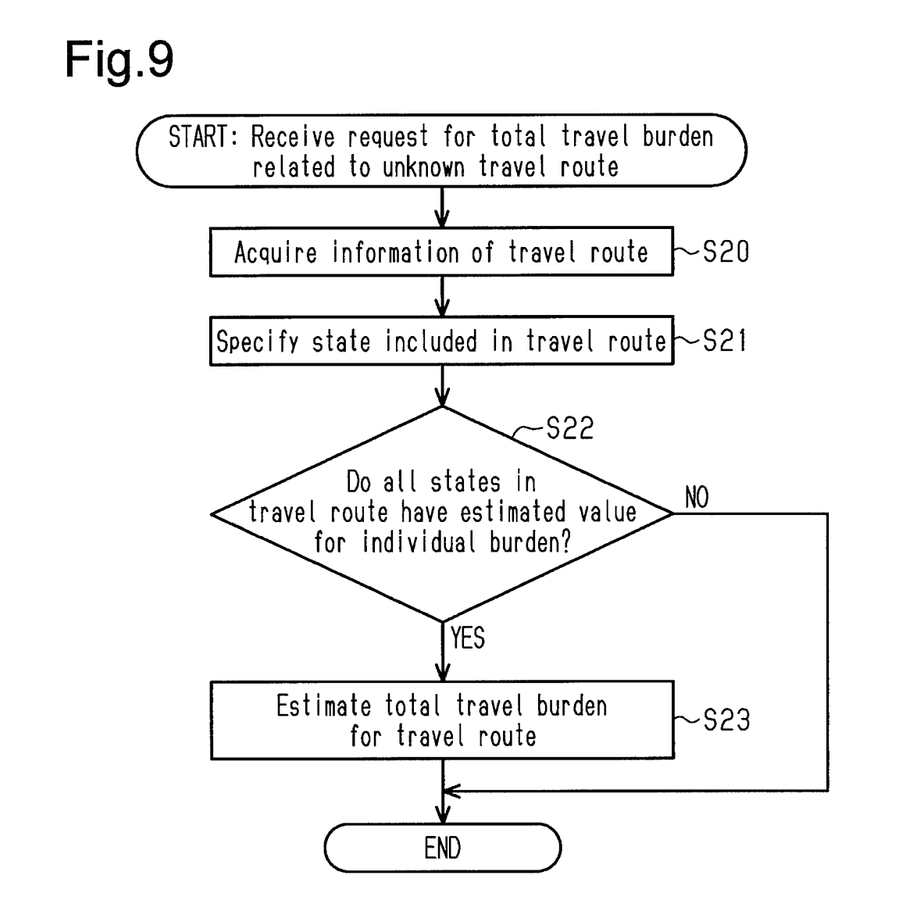
FIG. 9 is a flowchart illustrating a burden estimation process for an unknown travel route executed by the burden estimation device of FIG. 1.

First, as illustrated in FIG. 9, the center 100 acquires information regarding the unknown travel route from the portable information terminal 200 (step S20).

Then, the center 100 specifies the states included in the unknown travel route acquired in step S20 using the state defining unit 111 by referring to the characteristic amounts defined in the state space table 121 (step S21). In this case, the center 100 predicts the characteristic amounts that are difficult to strictly recognize before the user travels, such as the weather, temperature, and pattern of use, from the characteristic amounts that define the states based on the latest information such the weather forecast and how often a train has been used.

Subsequently, the center 100 determines whether or not the individual burden estimation value is stored in the storage unit 120 for each state included in the unknown travel route using the total travel burden estimation unit 115 (step S22). In addition, if it is determined that the individual burden estimation value is not stored in the storage unit 120 for at least some the states included in the unknown travel route (NO in step S22), the center 100 ends the total travel burden estimation process of FIG. 9 without estimating the total travel burden of the unknown travel route.

If the center 100 determines that the estimated values of the individual burdens for all of the states included in the unknown travel route are stored in the storage unit 120 (YES in step S22), the center 100 adds the estimated values of the individual burden to estimate the total travel burden of the unknown travel route with the total travel burden estimation unit 115 (step S23). Further, the center 100 transmits the total travel burden estimated in this manner to the portable information terminal 200 of the requesting user and then terminates the total travel burden estimation process of FIG. 9.

Next, specific procedures for processing a going-out preference calculation process executed by the center 100 according to this embodiment will be described in detail. When a request for a going-out preference is received from a user using the portable information terminal 200, the center 100 executes the going-out preference calculation process in response to the request.

Figure 10:
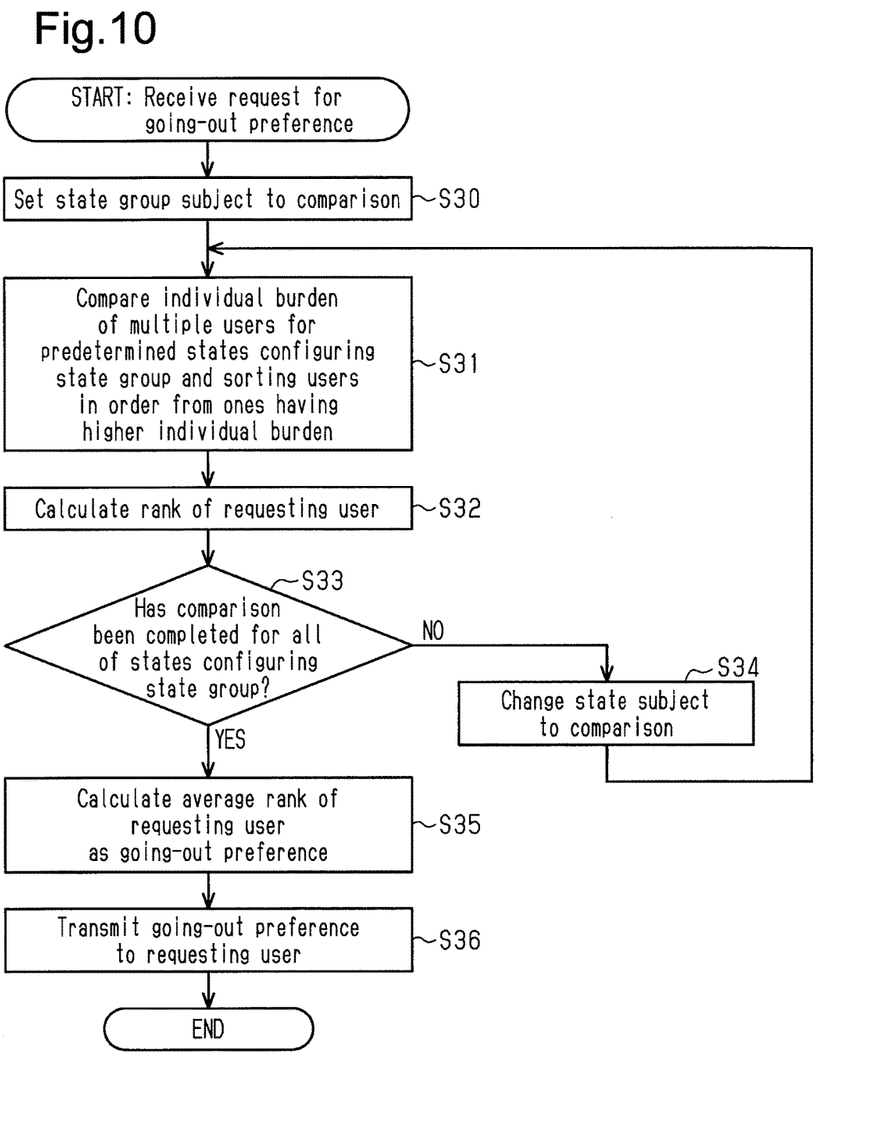
FIG. 10 is a flowchart illustrating a going-out preference calculation process executed by the burden estimation device of FIG. 1.

First, as illustrated in FIG. 10, the center 100 sets a state group including a plurality of states used in calculation of the going-out preference with the going-out preference calculation unit 116 (step S30).

Then, the center 100 reads individual burdens of a plurality of users from the storage unit 120 with the going-out preference calculation unit 116 for a predetermined state included in the state group. In addition, the center 100 sorts the users in order from the higher individual burden using the going-out preference calculation unit 116 based on the individual burden of the plurality of users read from the storage unit 120 (step S31). Furthermore, the center 100 calculates the rank of the requesting user using the going-out preference calculation unit 116 by referring to the order of the user sorted in preceding step S31 (step S32).

If the comparison of the individual burden of the user has not been completed for all of the states included in the state group (NO in step S33), the center 100 selects a state of the comparison of the individual burden of the user from the states included in the state group (step S34). Then, the center 100 returns to step S31 and repeats steps S31 to S34 until the comparison of the individual burden of the user is completed for all of the states included in the state group.

Then, if it is determined that the comparison of the individual burden of the user is completed for all of the states included in the state group (YES in step S33), the center 100 calculates an average value of the rank of the user calculated in step S32 for a plurality of states included in the state group as the going-out preference with the going-out preference calculation unit 116 (step S35). In addition, the center 100 transmits the going-out preference calculated in this manner to the portable information terminal 200 of the requesting user (step S36). Then, the center 100 ends the going-out preference calculation process for the user illustrated in FIG. 10.

Next, the operation of the center 100 according to this embodiment will be described by particularly focusing on the effect of estimating the total travel burden of the user regarding the unknown travel route in response to a request from a user owning the portable information terminal 200.

Generally, the burden of a user who is traveling using a plurality of methods of travel does not necessarily reflect the physical consumption level of the user. For example, the psychological state of the user when traveling through a travel section differs in accordance with whether the user is traveling for commuting or for a private purpose. Therefore, the burden on the user may change significantly in certain cases.

The burden on the user also significantly depends on the psychological situation of the user in addition to the physical consumption level of the user as described above. Thus, there is a limit to accurately detecting the burden on the user when using biological signals of the user. For this reason, it is preferable that the burden on the user be evaluated through a directly inquiry to the user by, for example, performing a dialog with the user. However, if the burden on the user is inquired whenever the user travels through the travel section, this would cause inconvenience.

In the present embodiment, in principle, the center 100 does not inquire the user about the burden whenever the user travels through a travel section. Rather, the center 100 inquires the user about the total travel burden when the user arrives at the destination of the travel route. This reduces the frequency of inquiry made to the user with regard to the burden. This improves the user convenience. The content of the total travel burden inquired to the user is not the burden of each travel section of the travel route. Rather, the content is the burden on the user for the entire travel route. Thus, the user does not need to remember the burden for each travel section until the user arrives at the destination of the travel route. This also improves user convenience.

The center 100 equally divides the total travel burden obtained through the inquiry to the user by the number of states included in the travel route to estimate the individual burden for each state. Then, the estimated values of the individual burden for the states included in the travel route are accumulated as the user repeatedly travels. Accordingly, the estimated value of the burden for each state approaches the ideal value that is in accordance with the actual situation of the user. As a result, even for an unknown travel route along which the user has not traveled in the past, the burden on the user can be recognized in advance by adding the burden estimation values of the states that correspond to the travel sections in the travel route.

As described above, the aforementioned embodiment has the advantages described below.

(1) The individual burden on the user corresponding to each state is estimated by performing reinforcement learning by setting the total travel burden, which is a comprehensive burden on the user who has shifted through a number of states, as a reward without the need to acquire data on the individual burden from the user whenever the state shifts because of a change in the method of travel. In addition, even when the user sets an unknown route as the travel route, the total travel burden on the user when traveling along the unknown travel route can be estimated by combining the individual burdens that have been already estimated.

(2) The levels of individual burdens of a plurality of users stored in the storage unit 120 are compared for each of the states included in the state group. Further, the going-out preference is calculated under the assumption that a user having a relatively smaller individual burden prefers to go out. In this manner, under the same circumstances, the burden level of a certain user is compared with that of another user. In addition, based on the comparison, the level of user preference to go out can be calculated as a new index referred to as the going-out preference.

(3) If the dispersion of the estimated values of the individual burden is relatively large, that is, if the dispersion of the individual burden estimation value is greater than a predetermined threshold value, the reliability of the individual burden estimation value is considered to be low. Therefore, data related to the individual burden are acquired from the user when the user shifts to the corresponding state. As a result, it is possible to improve the reliability of the estimated values of the individual burden for the states included in the state space. In addition, it is possible to estimate the total travel burden of the user with high reliability when an unknown route is set as the travel route of the user.

(4) If the individual burden is unknown for some of the states included in the travel route of the user, the reliability of the estimated total travel burden is low when a user travels along a travel route including such states. If a travel route includes a state in which the individual burden of the user is unknown, the data related to the individual burden in such a state is acquired from the user as the user travels along the travel route. As a result, data related to the individual burden is obtained in a pinpoint manner for a state in which the individual burden is unknown in the travel route of the user. Therefore, the individual burdens of the states included in the state space are calculated in a further suitable manner. This allows the total travel burden of the user for a case where an unknown route is set as a travel route to be estimated with high reliability by adding the individual burdens of the states included in this travel route.

(5) If the travel route is often used by the user and the data related to the individual burdens of each state included in the travel route has most likely been sufficiently obtained, the total travel burden does not necessarily have to be acquired from the user when the user arrives at the destination of the travel route. This reduces unnecessary burden on the user while collecting a large amount of data related to the individual burdens of the states included in the state space.

The aforementioned embodiments may be modified as described below.

In the aforementioned embodiment, if it is considered that the frequency of the occurrence of the states included in a travel route is relatively high and the user frequently uses the travel route, the history learning unit 112 instructs the portable information terminal 200 to have a dialog with the user at a frequency of once out of a number of times when the user arrives at the destination of the travel route. Instead, the history learning unit 112 may instruct the portable information terminal 200 to have a dialog with the user whenever the user uses the travel route regardless of the frequency of the occurrence of the states included in the travel route. In this configuration, the total travel burden of the user regarding the travel route frequently used by the user is updated to the latest information at a high frequency. This further improves the reliability of the data on the burden of the user in the states included in the travel route.

In the aforementioned embodiment, the total travel burden estimation unit 115 is configured to estimate the total travel burden for an unknown travel route only when the estimated values of the individual burden are obtained for all of the states included in this unknown travel route. Alternatively, the total travel burden estimation unit 115 may estimate the total travel burden for the unknown travel route even when the individual burden estimation value has not been obtained for some of the states included in the unknown travel route. The individual burden of the state for which the individual burden estimation value has not been obtained may be calculated based on the estimated value of the individual burden for a state in which the individual burden has been obtained. For example, the individual burden of a state for which the estimated value of the individual burden has not been obtained may be calculated based on the difference between the characteristic amount of a state for which the estimated value of the individual burden has been obtained and the characteristic amount of a state for which the estimated value of the individual burden estimation value has not been obtained. For example, if there are two states for which only the usage time serving as the characteristic amount differs from each other, the individual burden of one state may be calculated from the individual burden of the other state in proportion to the usage time. In addition, the estimated value of the individual burden may be calculated by setting the weighting factor in accordance with the characteristic amount that defines a state other than the usage time.

In the aforementioned embodiment, if a state in which the individual burden of the user is unknown is included in the travel route, the history learning unit 112 is configured to inquire the user on the individual burden for an unknown state when the user shifts to a state in which the individual burden is unknown. Alternatively, if a state in which the individual burden of the user is unknown is included in the travel route, the history learning unit 112 may be configured to also inquire the user of the individual burden corresponding to the unknown state in addition to the total travel burden for the entire travel route when the user arrives at the destination of the travel route.

The history learning unit 112 may inquire the user of the total travel burden of the entire travel route only when the user arrives at the destination of the travel route regardless of whether or not a state in which the individual burden of the user is unknown is included in the travel route.

In the aforementioned embodiment, if the dispersion of the estimated values of the individual burden corresponding to the current state of the user is relatively large, the history learning unit 112 is configured to instruct the portable information terminal 200 to have a dialog with the user in order to inquire the individual burden corresponding to the current state of the user. Alternatively, the history learning unit 112 may be configured to inquire the user of the total travel burden for the entire travel route only when the user arrives at the destination of the travel route regardless of the dispersion of the estimated values of the individual burden corresponding to the current state of the user. In this case, the function for calculating the dispersion of the estimated values of the individual burden may be omitted from the control unit 110 of the center 100. In addition, the individual burden estimation unit 113 may be configured to update the data on the estimated values of the individual burden stored in the storage unit 120 by rewriting the storage unit 120 with the latest data whenever the estimated value of the individual burden is obtained without recording the estimated value as log data to the storage unit 120 whenever the individual burden of each state is estimated.

In the aforementioned embodiment, the going-out preference calculation unit 116 is configured to calculate the average value of the user rank for a plurality of individual burdens included in the state group as a going-out preference. However, the going-out preference calculation unit 116 may be configured to calculate the going-out preference of the user based on any function computation using the individual burdens of the states included in the state group.

In the aforementioned embodiment, the going-out preference calculation unit 116 is configured to compare the levels of the individual burden of the users stored in the storage unit 120 for a state group including a plurality of states and calculate the going-out preference under the assumption that a user who has a relatively smaller individual burden prefers to go out. Alternatively, the going-out preference calculation unit 116 may be configured to calculate the going-out preference by comparing the levels of the individual burdens of the users for a single state.

In the aforementioned embodiment, the individual burden estimation unit 113 is configured to evaluate the burden of the user based on the dialog input history 123 input from the user using the portable information terminal 200. Alternatively, the history learning unit 112 may be configured to use data on burdens directly input from the user using the portable information terminal 200 as the evaluation data.

In the aforementioned embodiment, the individual burden estimation unit 113 executes the Monte Carle method as one of the reinforcement learning methods by taking into account the total travel burden of the user in order to estimate the individual burden for each state included in the travel route. However, the individual burden estimation unit 113 may execute the temporal difference (TD) learning method as the reinforcement learning method. The TD learning method is faster than the Monte Carle method but is not reliable when the learning value is based on an unknown state or a small number of samples. Therefore, as described above, it is important to check the reliability of the individual burden for each state based on the dispersion or the like of the estimated values of the individual burden for each state as described above. Furthermore, the individual burden estimation unit 113 may execute a dynamic programming method as the reinforcement learning method if the possibility of shifting between states included in the state space is recognized in advance.

It should be apparent to those skilled in the art that the present invention may be embodied in many other specific forms without departing from the spirit or scope of the invention. Therefore, the present examples and embodiments are to be considered as illustrative and not restrictive, and the invention is not to be limited to the details given herein, but may be modified within the scope and equivalence of the appended claims.

The invention claimed is:

1. A burden estimation device comprising:
circuitry including a storage unit for storing programs and a control unit for executing the programs stored in the storage unit, the control unit configured to control:
   a state space configuration unit that defines a state space, wherein the state space is defined in correspondence with a travel route along which a user travels to a destination while changing methods of travel, the state space includes states that correspond to the travel route along which the user travels and in which the states are continuous over time, each of the states is defined by combining multiple types of data that characterize burden on the user as the user travels;
   a history learning unit configured to acquire from the user and store in a storage unit data related to the burden on the user when the user travels to the destination along the travel route;
   an individual burden estimation unit configured to evaluate a total travel burden as a comprehensive burden on the user when the user travels to the destination along the travel route based on the data related to the burden stored in the storage unit, and the individual burden estimation unit is further configured to estimate an individual burden that is the burden on the user in correspondence with each of the states included in the state space through reinforcement learning that sets the total travel burden as a reward; and
   a total travel burden estimation unit configured to estimate the total travel burden corresponding to an unknown travel route based on the estimated individual burden if the unknown travel route is set and the individual burden has already been estimated for at least some of the states defined in correspondence with the unknown travel route, wherein
   the user sets the travel route using a portable information terminal and the history learning unit instructs the portable information terminal to have a dialog with the user when the user arrives at destination of the set travel route.

2. The burden estimation device according to claim 1, wherein if the individual burden has already been estimated for every one of the states defined in correspondence with the unknown travel route, the total travel burden estimation unit is configured to set a sum of the estimated individual burdens as the total travel burden corresponding to the unknown travel route.

3. The burden estimation device according to claim 1, wherein the individual burden estimation unit is configured to store an estimated value of the individual burden corresponding to each of the states for a plurality of users in the storage unit as learning data, and the burden estimation device further comprising a going-out preference calculation unit configured to compare levels of the individual burdens of the users for one or more states and calculate, based on the comparison, a going-out preference indicating that a user having a relatively smaller individual burden prefers to go out.

4. The burden estimation device according to claim 1, wherein
   the individual burden estimation unit is configured to store an estimated value of the individual burden corresponding to each of the states in the state space as learning data in the storage unit, and
   if a dispersion of the estimated values of the individual burden for one of the states stored in the storage unit is greater than or equal to a predetermined threshold value, the history learning unit is configured to acquire data related to the individual burden of the state from the user.

5. The burden estimation device according to claim 1, wherein if an estimated value of the individual burden is not obtained for some of the states defined in correspondence with the travel route, the history learning unit is configured to acquire data related to the individual burden for those some of the states from the user while the user is traveling along the travel route.

6. The burden estimation device according to claim 1, wherein if a frequent level of the travel route is greater than or equal to a predetermined threshold value, the history learning unit is configured to acquire data related to the burden from a user at a frequency of once out of a number of times when the user reaches the destination of the travel route.

7. A method for estimating burden, the method comprising:
   defining a state space, wherein the state space is defined in correspondence with a travel route along which a user travels to a destination while changing methods of travel, the state space includes states that correspond to the travel route along which the user travels and in which the states are continuous over time, each of the states is defined by combining multiple types of data that characterize burden on the user as the user travels;
   acquiring, from the user, and storing, in a storage unit, data related to the burden on the user when the user travels to the destination along the travel route;
   evaluating a total travel burden as a comprehensive burden on the user when the user travels to the destination along the travel route based on the data related to the burden stored in the storage unit;

estimating an individual burden that is the burden on the user in correspondence with each of the states included in the state space through reinforcement learning that sets the total travel burden as a reward; and estimating the total travel burden corresponding to an unknown travel route based on the estimated individual burden if the unknown travel route is set and the individual burden has already been estimated for at least some of the states defined in correspondence with the unknown travel route, wherein the user sets the travel route using a portable information terminal, a history learning unit instructs the portable information terminal to have a dialog with the user when the user arrives at destination of the set travel route.

8. A burden estimation device comprising circuitry, the circuitry comprising:

a storage unit for storing programs and a control unit for executing the programs stored in the storage unit, the control unit configured to:

define a state space, wherein the state space is defined in correspondence with a travel route along which a user travels to a destination while changing methods of travel, the state space includes states that correspond to the travel route along which the user travels and in which the states are continuous over time, each of the states is defined by combining multiple types of data that characterize burden on the user as the user travels;

acquire, from the user, and store, in a storage unit, data related to the burden on the user when the user travels to the destination along the travel route;

evaluate a total travel burden as a comprehensive burden on the user when the user travels to the destination along the travel route based on the data related to the burden stored in the storage unit;

estimate an individual burden that is the burden on the user in correspondence with each of the states included in the state space through reinforcement learning that sets the total travel burden as a reward; and estimate the total travel burden corresponding to an unknown travel route based on the estimated individual burden if the unknown travel route is set and the individual burden has already been estimated for at least some of the states defined in correspondence with the unknown travel route, wherein the user sets the travel route using a portable information terminal and the control unit instructs the portable information terminal to have a dialog with the user when the user arrives at destination of the set travel route.

* * * * *